United States Patent [19]

Lew et al.

[11] Patent Number: 5,181,505
[45] Date of Patent: Jan. 26, 1993

[54] METHOD AND APPARATUS FOR DELIVERY OF A MEDICAMENT IN THE ORAL CAVITY

[76] Inventors: Chel W. Lew, 9218 Old Homestead, San Antonio, Tex. 78230; Thomas B. Aufdemorte, 1638 Vista del Monte, San Antonio, Tex. 78216; Howard S. McGuff, 3226 Falcon Grove, San Antonio, Tex. 78247; Gerald L. Alderson, 114 Cherokee La., San Antonio, Tex. 78232

[21] Appl. No.: 726,628
[22] Filed: Jun. 28, 1991

Related U.S. Application Data

[63] Continuation of Ser. No. 320,500, Mar. 8, 1989, abandoned.
[51] Int. Cl.⁵ .............................. A61M 16/00
[52] U.S. Cl. ............... 128/200.26; 128/207.15; 604/57; 604/77; 604/265; 604/285
[58] Field of Search ............ 604/54, 57, 77, 93, 604/174, 257, 259, 265, 285, 286, 288, 890.1, 891.1, 892.1; 128/DIG. 26, 200.26, 207.14, 207.15, 207.17

[56] References Cited

U.S. PATENT DOCUMENTS

| | | |
|---|---|---|
| 1,767,785 | 6/1930 | Sushko .................. 604/288 |
| 2,020,107 | 11/1935 | Cruickshank . |
| 3,173,418 | 3/1965 | Baran . |
| 3,545,439 | 12/1970 | Duncan . |
| 3,566,874 | 3/1971 | Shepherd et al. . |
| 3,736,939 | 6/1973 | Taylor .................. 604/265 |
| 3,783,868 | 1/1974 | Bokros . |
| 3,844,285 | 10/1974 | Laby . |
| 3,927,676 | 12/1975 | Schultz . |
| 3,975,350 | 8/1976 | Hudgin et al. . |
| 3,995,633 | 12/1976 | Gougeon . |
| 4,055,178 | 10/1977 | Harrigan . |
| 4,159,720 | 7/1979 | Burton . |
| 4,177,256 | 12/1979 | Michaels et al. . |
| 4,198,965 | 4/1980 | Strickman et al. . |
| 4,206,757 | 6/1980 | Grandadam et al. . |
| 4,219,016 | 8/1980 | Drobish et al. . |
| 4,235,236 | 11/1980 | Theeuwes . |
| 4,286,587 | 9/1981 | Wong . |
| 4,309,996 | 1/1982 | Theeuwes . |
| 4,312,347 | 1/1982 | Magoon et al. . |
| 4,326,515 | 4/1982 | Shaffer et al. . |
| 4,327,725 | 5/1982 | Cortese et al. .................. 604/57 |
| 4,344,428 | 8/1982 | Sherman .................. 100/DIG. 26 |
| 4,369,773 | 1/1983 | Chvapil . |
| 4,417,576 | 11/1983 | Baran .................. 100/207.15 |
| 4,479,795 | 10/1984 | Mustacich et al. . |
| 4,506,680 | 3/1985 | Stokes . |
| 4,515,593 | 5/1985 | Norton . |
| 4,520,813 | 6/1985 | Young . |
| 4,526,578 | 7/1985 | Wong . |
| 4,577,642 | 3/1986 | Stokes . |
| 4,589,880 | 5/1986 | Dunn et al. . |
| 4,627,851 | 12/1986 | Wong et al. . |
| 4,627,852 | 12/1986 | von Bittera et al. . |
| 4,629,449 | 12/1986 | Wong . |
| 4,640,689 | 2/1987 | Sibalis . |
| 4,655,766 | 4/1987 | Theeuwes et al. . |
| 4,693,243 | 9/1987 | Buras .................. 604/265 |
| 4,769,013 | 9/1988 | Lorenz et al. .................. 604/265 |
| 4,863,457 | 9/1989 | Lee .................. 604/891.1 |
| 4,888,074 | 12/1989 | Pocknell .................. 604/892.1 |

FOREIGN PATENT DOCUMENTS 1069826 1/1984 U.S.S.R. .

Primary Examiner—C. Fred Rosenbaum
Assistant Examiner—Mark W. Bockelman
Attorney, Agent, or Firm—Vaden, Eickenroht, Thompson, Boulware & Feather

[57] ABSTRACT

An apparatus (10) for dispensing a medicament such as an antibiotic in the upper aerodigestive tract of an intubated patient (22). The apparatus (10) is a generally ovoid body (12) comprised of a substrate which can be polymeric, natural or synthetic woven or spun fiber, a gel, or other substance capable of being impregnated with the medicament and then releasing the medicament when contacted by an aqueous solution, specifically, the saliva of patient (22).

Body (12) is shaped with rounded tapered surfaces (30) and ends (26) for engaging the mucosa of the alveolar ridge (32) and palate (20) of patient (22) to stabilize the apparatus (10) in the oral cavity (24). A channel (38) is provided for passage of the tube (40) of an endotracheal tube (36) therethrough which cooperates with the surfaces (30) and ends (26) to stabilize both endotracheal tube (36) and body (12) in the oral cavity (24).

22 Claims, 2 Drawing Sheets

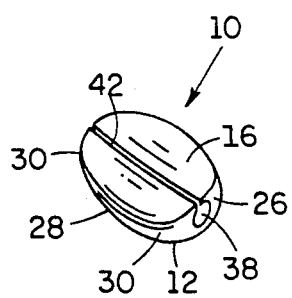
FIG. 1a
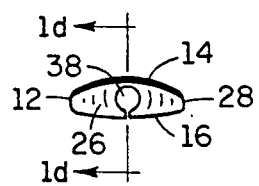
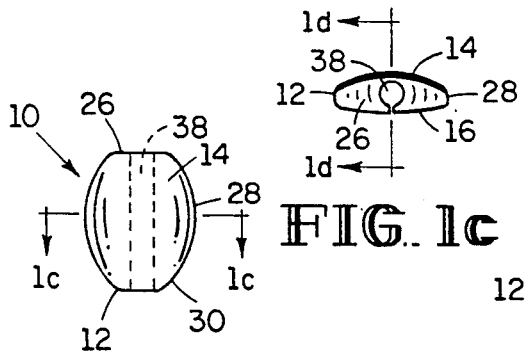
FIG. 1b  FIG. 1c
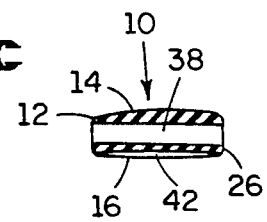
FIG. 1d
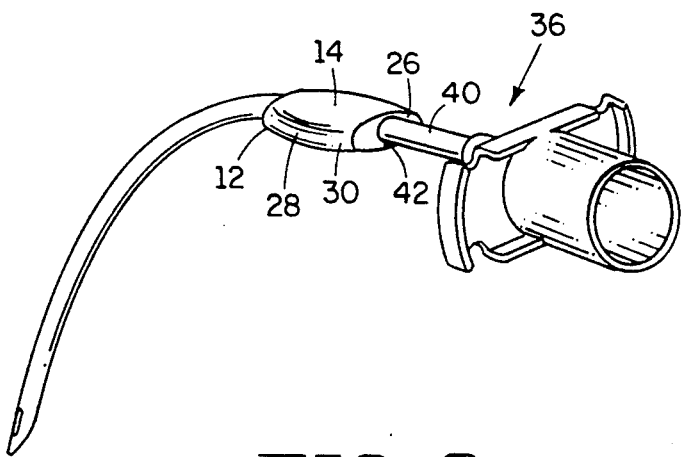
FIG. 2
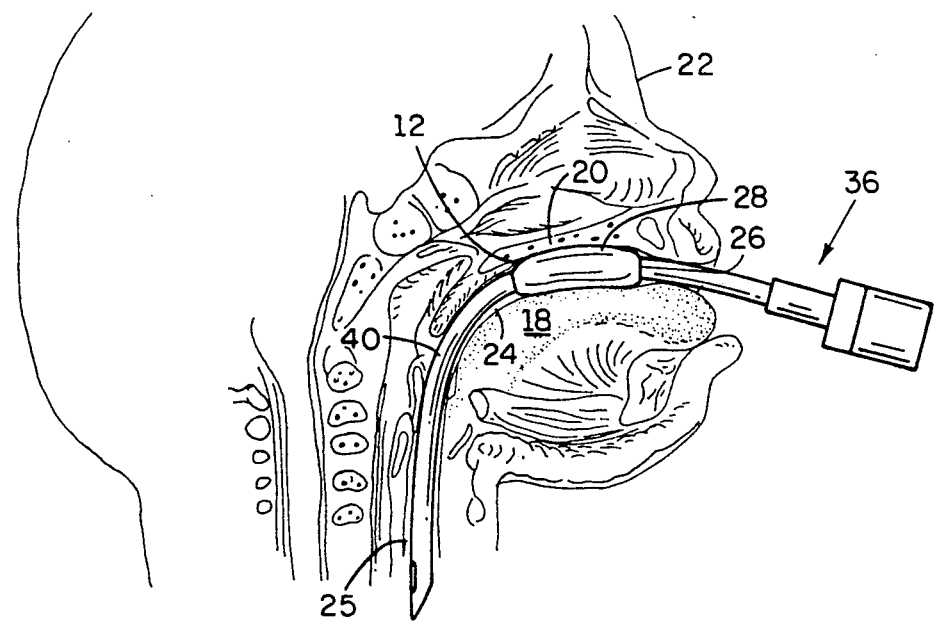
FIG. 3

METHOD AND APPARATUS FOR DELIVERY OF A MEDICAMENT IN THE ORAL CAVITY

This application is a continuation of co-pending application Ser. No. 07/320,500, filed on Mar. 8, 1989, now abandoned.

BACKGROUND OF INVENTION

The present invention relates to a device which delivers a medicament in the upper aerodigestive tract, and specifically, to the oral cavity. More particularly, the present invention relates to an appliance for delivering antibiotics, topical steroids, local anesthetics and other medicaments in the upper aerodigestive tract at therapeutically effective dosage levels which also stabilizes an endotracheal tube extending therethrough and which is sized and dimensioned so as to be stabilized in the oral cavity by engagement of the tongue and the mucosa of the oral cavity.

Recent advances in medical science have led to a proliferation of invasive monitoring methodologies and therapeutic techniques. Such techniques include endotracheal and nasogastric tubes and urinary, arterial, venous, cardiac and pulmonary artery catheters. Prosthetic and therapeutic implant devices, such as vascular and central nervous shunts, orthopaedic-dental implants, and pacemakers have also become common.

With these advances, complications have also arisen; the primary complication is infection. Statistics indicate that forty-five percent of the 2,000,000 nosocomial infections that occur annually in the United States are device related. Measures such as local care and systemic antibiotics have proven less than totally effective in preventing such infections.

In addition, current therapeutic modalities for the treatment of patients with ulcerative and vesicula-bullous lesions involving oral mucosa are ineffective. The most troublesome of these conditions are recurrent aphthous stomatitis, lichen planus, pemphigus vulgaris, oral mucous membrane pemphigoid, lichenoid drug eruption, hypersensitivity mucositis, and traumatic mucositis. Many of these conditions show a favorable, often dramatic, response to topical and/or systemic steroid therapy. Most, however, do not justify administration of systemic steroids.

Although topical steroids offer an alternative mode of therapy for such lesions, their use has been less than satisfactory due to the inability to maintain intimate contact of the pharmacologic agent against the involved lesion for a therapeutically effective period of time due to the moist nature of the oral environment. Some efforts to overcome this problem have been made using mucoadhesives such as ORABASE (tm). Although widely used, these agents are generally less than optimal in their efficacy due to the salivary flow and motion associated with speech, mastication, and deglutition, all of which tend to rapidly dilute and/or eliminate the active medicament. In addition, the anatomical features and location of many mucosal lesions limit the ability to apply topical agents to the involved area.

Attempts have been made to provide devices which overcome such problems. Illustrative are certain prior art references which disclose the incorporation of medicaments such as antimicrobials into biocompatible polymers, and the fashioning of such polymers into invasive and/or indwelling devices. For instance, U.S. Pat. No. 4,479,795 (Mustacich, et al.) describes a polymer having an antimicrobial agent releasably incorporated therein said to be capable of being used for the manufacture of urinary and intravenous catheters, the antimicrobial agent diffusing from the polymer to inhibit bacterial infection once the device is in place. Similarly, U.S. Pat. No. 4,309,996 (Theeuwes) describes a drug delivery system consisting of a microporous wall surrounding a compartment containing a drug which releases the drug in a fluid environment. However, such references lack any teachings of how to deliver an effective dosage of the incorporated medicament in the upper aerodigestive tract while also stabilizing the device into which the medicament is incorporated in the patient's oral cavity once it is inserted.

Also of interest are U.S. Pat. Nos. 3,566,874 (Shepherd, et al.) and 4,515,593 (Norton). The Shepherd, et al. patent discloses a catheter coated with a hydrophilic acrylate or methacrylate polymer that is said to reduce the irritation and infection accompanying the use of catheters and which can be absorbed with an antibiotic. Norton describes a catheter having a portion of the exterior surface coated with a hydrophilic elastomer for reception of a microbicide. These references likewise lack a teaching of the delivery of a therapeutically effective dose of the medicament in the upper aerodigestive tract while also stabilizing the device in the oral cavity of the patient.

Certain prior art does appear to teach stabilizing an indwelling device in the patient. For instance, U.S. Pat. Nos. 4,326,515 (Shaffer, et al.), 4,520,813 (Young) and 3,927,676 (Schultz) describe external devices for securing an endotracheal tube in place in the oral cavity of a patient. The effectiveness of such devices can be summed up by stating that, so far as is known, it is often necessary to use adhesive tape, in addition to the device, to adequately stabilize the endotracheal tube. Further, those references include no suggestion whatsoever of delivering an effective dose of a selected medicament in the upper aerodigestive tract, much less the topical application of the medicament to the mucosa of, for instance, the oral cavity.

In sum, all the devices of which Applicants are aware are characterized by one or more limitations such that there is a need for an apparatus and method for topical drug therapy for conditions including, but not limited to, infections associated with indwelling appliances such as nasogastric and endotracheal tubes, the lesions listed above, oral and/or pharyngeal tumors, viral eruptions, and any other condition which benefits from the high concentrations of an appropriate medicament that can be maintained in intimate contact with the involved tissue(s) over prolonged and controlled periods of time. It is, therefore, an object of the present invention to provide such an apparatus.

Another object of the present invention is to provide an intraoral drug delivery appliance containing neat and/or encapsulated antimicrobial agent(s) to provide sustained release of the agent(s) at antimicrobially effective levels.

Another object of the present invention is to reduce or eliminate infection associated with the use of indwelling appliances in the upper aerodigestive tract.

Another object of the present invention is to provide an apparatus for delivery of a medicament in the upper aerodigestive tract which can be introduced or removed from the oral cavity of an intubated patient without extubating the patient.

Still another object of the present invention is to provide an apparatus which is capable of topical application of a medicament to the mucosa of the oral cavity or to other specific locations in the upper aerodigestive tract of the patient.

Another object of the present invention is to provide a method and apparatus for stabilizing an endotracheal tube in the oral cavity of a patient.

Other objects, and the advantages, of the present invention will be made clear by the following description of the presently preferred embodiments of appliances constructed in accordance with the invention.

SUMMARY OF THE INVENTION

These objects are accomplished by providing an apparatus for delivery of a medicament in the upper aerodigestive tract of a patient comprising a body formed of a substrate capable of being impregnated with a medicament to be delivered in the upper aerodigestive tract of the patient having means formed therein for stabilizing the body by engagement of the mucosa of the palate and alveolar ridge of the patient when placed on the tongue of the patient. The body is also provided with means for passage of an endotracheal tube therethrough, the passage means cooperating with the endotracheal tube and the stabilizing means to stabilize the body and the endotracheal tube in the oral cavity as a result of the engagement of the mucosa by the stabilizing means.

Also provided is a method of stabilizing an endotracheal tube in the oral cavity of an intubated patient while dispensing a topical medicament in the upper aerodigestive tract comprising placing a body comprised of a substrate impregnated with a medicament to be released in the upper aerodigestive tract onto the tongue of a patient and introducing an endotracheal tube into the oral cavity by passing the endotracheal tube through the body. The body is stabilized in the oral cavity by engagement of the mucosa of the palate and alveolar ridge, and saliva is allowed to circulate around the body to facilitate the release of the medicament from the body.

BRIEF DESCRIPTION OF THE DRAWINGS

FIG. 1a is a perspective view of the bottom of a presently preferred apparatus constructed in accordance with the present invention.

FIG. 1b is a top plan view of the apparatus of FIG. 1.

FIGS. 1c and 1d are sectional views taken along 1c—1c in FIG. 1b and 1d—1d in FIG. 1c, respectively.

FIG. 2 is a perspective view of the apparatus of FIG. 1 in place of an endotracheal tube.

FIG. 3 is a saggital section of the upper aerodigestive tract of a human patient showing the apparatus of FIG. 1 in use.

DETAILED DESCRIPTION OF THE INVENTION

Figure 4:
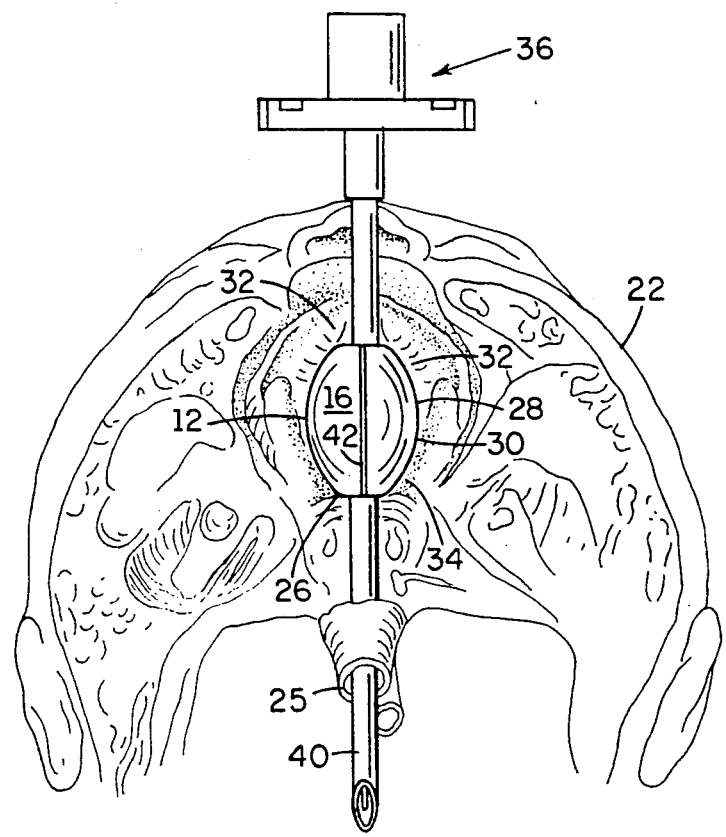
FIG. 4 is an inferior view of the roof of the mouth and the pharyngeal palate of a human patient showing some of the structures of the oral cavity on which the apparatus of FIG. 1 is stabilized in the oral cavity when in use.

Referring to FIGS. 1a–1d, a presently preferred embodiment of an apparatus constructed in accordance with the present invention is indicated generally at reference numeral 10. The apparatus 10 is comprised of a body 12 which is generally ovoid in shape, having top and bottom surfaces, reference numerals 14 and 16, respectively, for engagement of the tongue 18 and the mucosa of the pharyngeal palate 20 of patient 22 when placed in the oral cavity 24 (see FIGS. 3 and 4).

Figure 5:
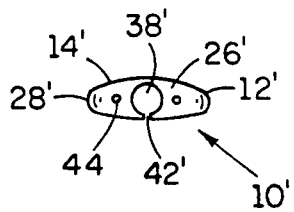
FIG. 5 is an end view of an alternative embodiment of the apparatus of FIG. 1.

Body 12 is formed of a substrate which is capable of being impregnated with a medicament to be delivered in the oral cavity 24 of patient 22. Appropriate substrates include any substance, preferably physiologically inert, which is capable of taking up the medicament and which will release the medicament with which it is impregnated when contacted by an aqueous solution such as saliva. The preferred substrate is a polymer, such as a cellulosic or other organic polymer or copolymer, which is at least somewhat resilient and can be molded in a desired shape, or shaped once formed into the generally ovoid preferred shape, and when impregnated with a medicament, will release that medicament at a dosage level high enough to be therapeutically effective for the desired purpose. Specifically, silicone elastomers such as those which are commercially available under the brand names OPTOSIL (tm), CUTTER-SIL (tm), and SILASTIC (tm) have been used as a substrate. Non-silicone containing polymers such as polyethylene have also been used successfully. As will be described below in connection with the description of FIGS. 5–7, the substrate may also take the form of a gel including the medicament or a sponge or other absorbent article which can be impregnated with the medicament.

Although it is sometimes desirable that the release of the impregnated medicament from the substrate approach a zero order release rate so that constant and/or specific dosages can be attained or maintained, such a release rate is not required. Substrates capable of any release rate which is therapeutically effective are appropriate for use in connection with the apparatus 10. For instance, studies conducted with substrates using various antibiotics as medicaments have shown that the concentration of the antibiotic released into an aqueous solution fluctuates by well over 100% over time depending upon such factors as the total wetted area of the body 12 formed from the substrate, the particle size of the antibiotic, whether the antibiotic is supplied "neat" (encapsulated), the type of polymer or other material comprising the substrate, and various other factors. Even such drastic fluctuations are acceptable as long as the minimum inhibitory concentration (MIC) of the antibiotic is maintained.

In one experiment, an aliquot of vancomycin was manually dispersed in sufficient OPTISIL (tm) that the antibiotic comprised 20% by weight of the mixture and the catalyst supplied commercially with that elastomer was then added. The mixture was poured into a mold to solidify into a body in the shape of the body 12. The concentration of vancomycin released from the molded body over time into a synthetic release fluid was then monitored by high performance liquid chromatography (HPLC). Analytical methods were adapted from procedures set out in the literature for vancomycin (Hoagland, R. J., et al., "Vancomycin: A rapid HPLC assay for a potent antibiotic," 8 J. Anal. Tox. 75-77 (1984); Jehl, F., et al., "Determination of vancomycin in human serum by high-pressure liquid chromatography," 27 Antimicrob. Agents Chemother. 503-507 (1985)) as well as for gentamycin (Albracht, J. H., et al., "Separation of gentamycin in raw material and pharmaceuticals by HPLC," Chromatogram, Jan. 1987, 7-8 (1987)), imipenem (Myers, C. M. et al., "Determination of imipenem and cilastatin in serum by high-pressure liquid chromatography," 26 Antimicrob. Agents Chemother. 78-81 (1984); Fravallese, D. A., et al., "Determination of imipenem (N-formimidoyl thienamycin) in human plasma and urine by high-performance liquid chromatography, comparison with microbiological methodology and stability." 310 J. Chromatogr. 71-84 (1984)), and ceftazidime (Fasching, C. E., et al., "High pressure liquid chromatographic analysis for quantitation of BMY-28142 and ceftazidime in human and rabbit serum," 9 J. Liq. Chromatogr. 1803-1814 (1986)). Within the first hour, the concentration of vanomycin in the release fluid had reached levels several times higher than the 25 μg/ml MIC, and the concentration of the antibiotic in the release field continued to increase, at slower rates, to 1500 μg/ml during the 25 hours over which concentration was monitored.

The experiment was then repeated using a 50% concentration of fine-particle size vanomycin in the same mold. Concentration of vancomycin in the release fluid rose slowly over approximately the first four hours to about 150 μg/ml and then dropped slowly over the next six hours. However, for at least about eight hours, the concentration of vancomycin was well above the 25 μg/ml MIC such that even the second experiment was conducted with a body 12 that was therapeutically effective and therefore would have been quite acceptable for the intended purpose, especially when the ease with which body 12 can be changed or the medicament replenished while patient 22 is intubated is considered. When the same experiment was repeated with 20% imipenem and 15% gentamycin, the results were similar to those obtained with 20% vancomycin, e.g., a rapid increase in concentration in the early hours which began to level off from 2-10 hours and then stayed essentially constant through 25 hours at levels in the range of 500-900 μg/ml.

The term "medicament" as used herein refers to any pharmacological agent which can be advantageously delivered in the upper aerodigestive tract and which is capable of being impregnated into the substrate. Appropriate medicaments for use in connection with the present invention include, but are not limited to, antibiotics, antioxidants, biocides, hormones, steroids, fungicides, vitamins, co-factors, anti-inflammatories, decongestants, antivirals, analgesics-antipyretics, anesthetics, anti-cancer and/or anti-tumor agents, immunostimulants, immunodepressants, monoclonal antibodies and/or other immunological agents, muscle relaxants, central nervous system stimulants or depressants, enzymes, detoxicants, antihistamines, and anti-metabolites. As set out below, the apparatus of the present invention has particular utility when the medicament is an antibiotic because bacterial infection is perhaps the greatest single hazard associated with the use of an indwelling device such as an endotracheal tube, especially in neonatal or immunocompromised patients. In those patients which are not immunocompromised, or in which the management of other clinical disorders is of primary importance, it is advantageous to use other medicaments. The apparatus of the present invention has particular application in patients who require topical application of a medicament to the mucosa of the oral cavity or to other specific location in the upper aerodigestive tract. For that reason, antibiotics, antivirals and anti-inflammatories, especially steroids, are preferred medicaments for use with the apparatus of the present invention.

Referring again to FIGS. 1a–1d, means is formed in body 12 for stabilizing body 12 in the oral cavity 24 of patient 22 in the form of the end and side surfaces, 26 and 28, respectively, of body 12. The end 26 and side 28 surfaces of body 12 are all relatively smooth and rounded so as not to present any rough edges when the body 12 engages the mucosa, the side surfaces 28 being tapered as shown at reference numeral 30. Body 12 is sized, and the sides 28 rounded and tapered at 30, to optimize engagement of the mucosa of the pharyngeal palate 20 and alveolar ridge 32 of patient 22 when body 12 is placed upon the tongue 18 and the mouth of patient 22 is closed. Further, as shown in FIG. 1c, the top surface 14 of body 12 is curved or arched. The curve in top surface 14 facilitates interdigitation of the body 12 and the slightly arched inferior aspect of the mucosa of the pharyngeal palate 20 when body 12 is positioned so as to be effectively "trapped" or contained between the anterior and lateral aspects of the alveolar ridge 32 as shown in FIG. 4. Stabilization is also provided by engagement of the lateral buccal mucosa by the tapered portion 30 of sides 28 as, for instance, at reference numeral 34. Alternatively, the stabilizing means may take the form of laterally extending "wings" (not shown) formed integrally or attached to body 12 which are clenched between the patient's teeth, projections which engage the gums posteriorally of the molars, or flanges which extend laterally and inferiorally to engage the lateral surfaces of the tongue. Other stabilizing means will be apparent to those skilled in the art who have the benefit of this disclosure.

Although stabilized in the oral cavity 24 by engagement of the tongue 18 and mucosa, the contact between body 12 and the mucosa of the oral cavity 24 preferably is not constant. Instead, the size and shape of body 12 provides sufficient clearance between the mucosa and body 12 to allow circulation of the saliva around body 12, even when the mouth of patient 22 is closed, to facilitate the release of the medicament from the substrate comprising body 12 and delivery of the medicament in the upper aerodigestive tract of the patient. Release of the medicament from body 12 by circulation of saliva therearound is so effective that if, for instance, the medicament is an antibiotic, bacterial infection can be eradicated from the upper aerodigestive tract, and the spread of such infection from the upper aerodigestive tract into the lungs (not shown) can be effectively checked.

Although sufficient clearance is provided around the body 12 to allow circulation of saliva therearound, the body 12 is quite efficient at application of a medicament to the mucosa of the oral cavity or to other specific locations of the upper aerodigestive tract, e.g., topical application of the medicament. Normal swallowing involves muscular activity throughout the oral cavity 24, invariably involving the tongue 18, and has the result of periodically pressing body 12 against the tongue 18 and the mucosa of the oral cavity 24. Because the tongue 18 and mucosa are generally moist as a result of normal salivation, each time one of the surfaces 14, 16, 26 or 28 contacts the tongue 18 or mucosa, medicament is delivered to that point of contact. This effect is enhanced in the case of neonatal patients who have reached sufficient age for development of the sucking reflex; suckling has the additional advantage of drawing the body 12 into the pharynx of the patient, without loss of stabilization, because of the movement of the tongue 18, on which body 12 rests, toward the pharynx, thereby making possible the topical application of the medicament to the pharyngeal mucosa; hence the use throughout this specification of the phrase "application of a medicament to the oral mucosa or to other specific locations of the upper aerodigestive tract". Further, even if body 12 does not contact the mucosa at a specific location, constant circulation of saliva during and between swallowing distributes the medicament throughout the upper aerodigestive tract with an efficiency which is difficult to achieve, if at all, with conventional treatment modalities. For these reasons, the apparatus 10 has particular application for application of medicaments to patients who are affected by conditions such as bacterial, fungal, or viral infections, ulcerative and vesicula-bullous lesions, or neoplastic growth in the upper aerodigestive tract, particularly the oral cavity or pharyngeal region.

The apparatus 10 is also provided with means formed in body 12 for passage of an endotracheal tube, indicated generally at reference numeral 36, therethrough. In the presently preferred embodiment shown in FIGS. 1 and 2, that tube passage means takes the form of channel 38. Although not necessary to the function of the apparatus 10, because the tube 40 of endotracheal tube 36 is passed through channel 38, channel 38 opens to the bottom surface 16 of body 12 through a slit 42. Slit 42 allows body 12, preferably formed from a substrate which is somewhat flexible and resilient, to be slipped onto and off of the tube 40 of endotracheal tube 36, the tube 40 residing in channel 38. Slit 42 is formed more narrowly than channel 38 to insure that tube 40 is retained within channel 38. The tube passage means cooperates with the endotracheal tube 36 passing therethrough to further stabilize the body 12 in the oral cavity 24 and to stabilize the endotracheal tube 36 as well.

Several alternative embodiments of the apparatus of the present invention are shown in FIGS. 5–8. To the extent possible, the structure of the embodiments shown in FIGS. 5–8 which functions in the same manner as the structure of the embodiment shown in FIGS. 1–4 is designated by the same reference numerals with a "prime" designation. In one alternative embodiment, shown in FIG. 5, the body 12' is provided with one or more ports 44 which are used for passage of a tube (not shown) other than the tube 40 of endotracheal tube 36 when the apparatus 10' is in place in the oral cavity of the patient. Ports 44 are used, for instance, for passage of a suction tube (not shown) for suctioning of the pharyngeal region of the patient without removing the apparatus 10' therefrom.

In the case of apparatus 10" (FIG. 6), body 12 comprises two pieces, basket 46 and substrate 48. One of the end surfaces 26" of basket 46, preferably the end 26" which will engage the mucosa of the anterior alveolar ridge 32 (see FIG. 4), is open to receive the substrate 48 therein. In all other respects, the shape of basket 46 is the same as that of body 12 (see FIGS. 1a–1d). Both basket 46 and substrate 48 are provided with a slit 42" for insertion of the tube 40" of an endotracheal tube into the channel 38" of substrate 48 when substrate 48 is positioned within basket 46.

Basket 46 is preferably constructed of semi-rigid, resilient, physiologically inert plastic or other polymeric material molded or constructed of strips woven so as to leave relatively large openings 50 between strips. Openings 50 allow engagement of the mucosa of the oral cavity 24 of the patient by substrate 48, and hence, application of the medicament with which substrate 48 is impregnated thereto. A semi-rigid material is preferred so that when basket 46 is placed on the tongue 18 and the tube 40" of an endotracheal tube passed therethrough, substrate 48 need only be slipped over tube 40" and slid down into the open end 26" of basket 46. The semi-rigid character of basket 46 insures that the end 26" remains open so that basket 46 effectively comprises a re-fillable pocket in the oral cavity 24 for dispensing a medicament therefrom. Basket 46 can also be comprised of a naturally occurring, proteinaceous substance, for instance, collagen fibers, chitin, or cartilage.

Substrate 48 is comprised of any of the materials listed above for the composition of the substrate of body 12. However, in the context of the apparatus 10" of FIG. 6, substrate 48 can also be comprised of an absorbent material such as a natural or synthetic sponge or a woven or spun natural or synthetic fiber. By way of example, a common synthetic sponge can be trimmed to size (because of the compressible nature of the sponge, exact fit is not even required), sterilized, absorbed with a solution of the desired medicament, and inserted into the basket 48. The sponge is preferably sized just slightly larger than basket 48 such that slight compression of the sponge is needed to insure that the sponge is secured within basket 46, but because substrate 48 is placed in basket 46 and basket 46 is positioned behind the anterior alveolar ridge 32 (see FIG. 4) to secure substrate 48 thereon, compression is not required.

Other examples of a material appropriate for use as substrate 48 are the spun synthetic fibers available under the brand name CELESTRA (tm) and the various, relatively tightly woven, highly absorbent cotton and cotton blend battings and fillers which are commercially available. Like a sponge, such substrates 48 have the additional advantage of having what amounts to inherent ports (not numbered) such as the ports 44 shown in the apparatus 10' in FIG. 5. Because of the rather loose construction of such materials, a small diameter tube (not shown) such as a suction tube can simply be forced through substrate 48 and one of the openings 50, the semi-rigid strips comprising basket 46 insuring that the openings 50 stay open sufficiently wide enough to permit passage of such a tube therethrough. The loose construction of such materials also provides an alternative embodiment of the above-described tube passage means. The substrate 48 can be inserted into basket 46 and tube 40" simply forced through substrate 48, there being no need to provide a channel 38" and slit 42" for passage of the tube 40" through substrate 48.

The two-piece, rather than monolithic, construction of the apparatus 10" also makes possible the use of additional materials for substrate 48. Because basket 46 effectively contains and supports substrate 48, substrate 48 can be comprised of less integral materials such as a gel or even a material much like a sugar-based hard candy, which dissolves in the same way a throat lozenge or cough drop dissolves, including the medicament. The gel can be an agar or gelatin-based gel, sodium alginate gel, or can be prepared by mixing an inexpensive, readily available, relatively inert protein such as serum albumin or collagen and the medicament together with glycerol or other highly viscous substance in high concentration, followed by drying to form an integral mass or lozenge. In any case, whether substrate 48 is sponge, fibrous, gel or dissolving, the relatively fast release of the medicament therefrom is not problemmatical because of the ease with which the substrate 48 can either be replaced, or in the case of a sponge or fibrous material, replenished with medicament while in place in basket 46 in the oral cavity simply by injecting the medicament into the sponge or fibrous material.

Figure 7:
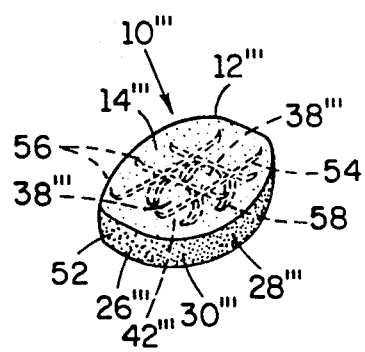
FIGS. 7 and 8 are perspective views of additional alternative embodiments of the apparatus of FIG. 1.

Referring now to FIG. 7, another apparatus 10''' is shown which includes a two-piece, or non-monolithic body 12'''. In the case of the apparatus 10''', the body 12''' is comprised of a substrate 52 supported on a framework 54. Framework 54 is comprised of a plurality of semi-rigid members having integral means for securing substrate 52 thereto in the form of the prongs 56 on which substrate 52 is impaled. The apparatus 10''' is provided with means for passage of an endotracheal tube (not shown) therethrough in the form of a semi-circular members 58 extending from framework 54 which define a slit 42''' and channel 38''', the semi-rigid nature of members 58 allowing the apparatus 10''' to be effectively snapped onto and off of the tube (not shown) of an endotracheal tube and slidable therealong.

Because of substrate 52 of the body 12''' of apparatus 10''' is external to the framework 54, as compared to being internal to the basket 46 of apparatus 10''' (see FIG. 6), substrate 52 is preferably more monolithic in character than the substrate 48 of apparatus 10''. For instance, substrate 52 may be comprised of a sponge into which prongs 56 will penetrate so that substrate 52 will be secured to framework 54. As was the case with the apparatus 10'' shown in FIG. 6, such a construction allows quick and convenient replacement of the substrate or replenishment of the medicament in the substrate in situ.

Figure 8:
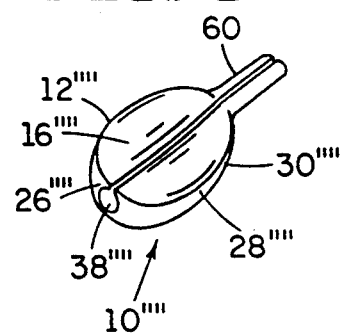

Because the apparatus of the present invention, by the shape and size of body 12 and engagement of the tongue 18 and mucosa of the oral cavity 21, is stabilized within the oral cavity 24, if it is desired to apply the medicament impregnated therein to the mucosa of the pharynx of the patient, body 12 is supplied with a pharyngeal extension such as the extension 60 shown on body 12'''' in FIG. 8. Pharyngeal extension 60 is preferably quite thin to avoid provoking the gag reflex of the patient and extends from the end 26'''' of body 12''' effectively serving as a jacket around a portion of the tube (not shown) of an endotracheal tube.

Using probes which are commercially available, in another embodiment of the apparatus of the present invention (not shown) the body 12 is used as an indwelling platform for probes for monitoring such physiological parameters as $pCO_2$, $pO_2$, pH, depth of inspiration, depth of expiration, respiratory rate, body temperature, and heart rate of the patient. Channel 38 provides a convenient conduit for passage of the leads of such probes into a tube and out of the patient's mouth to the associated instrumentation.

In reviewing FIGS. 3 and 4, those skilled in the art will recognize that no teeth are shown in the oral cavity 24 of patient 22. The teeth were omitted from those figures partly for purposes of clarity and partly because the apparatus 10 has particular utility for use with neonates. Because the immune system of the neonate is not well developed, such patients are particularly susceptible to infection associated with the use of indwelling devices.

An example of that utility is provided by the case history of a neonatal baboon with which the apparatus 10 was used. The neonatal baboon is an appropriate model for study because of the similar sizes of the animal and human neonates (the endotracheal tubes used for human neonates, for instance, are the proper size and configuration for use on baboon neonates) and because both are afflicted by similar infections and clinical disorders. Immediately after the baboon was born, it was intubated with an endotracheal tube stablized by an apparatus shaped as the apparatus 10 shown in FIGS. 1–4, and impregnated with 20% by weight gentamycin. Within four days, cultures taken from the oral cavity of the baboon were positive for *Staphylococcus epidermidis*, and screening studies indicated that the *S. epidermidis* strain was resistant to gentamycin.

The apparatus impregnated with gentacymin was then removed and replaced with a similar apparatus impregnated with 20% vancomycin. With two days, cultures from the oral cavity indicated that the colonization had dropped from 185 colony forming units (CFU) at four days to 0 CFU. At sixteen days, cultures from the oral cavity indicated no *S. epidermidis* infection and cultures from the trachea indicated that the infection had been almost eradicated from that location. Administration of the antibiotic in this fashion was so effective that infection levels were below those of control baboons maintained on antibiotics such as gentamycin and vancomycin given intravenously.

Even though neonates do, of course, increase in size such that an apparatus 10 sized for use in the oral cavity of a five-day old patient is not sized for maximum stabilization when used in a five-year old patient, for a variety of reasons, it is not necessary to custom build the apparatus 10 for every patient. One reason is that the oral cavity, being part of the patient's head, which does not change sizes as drastically as the rest of the body, does not change in dimension as quickly or as much as the rest of the body as the patient grows. Secondly, an exact fit in the oral cavity is not required; the body 12 needs only to be stabilized in the oral cavity by engagement of the mucosa when displaced in one direction or another (e.g., captured by the anatomical configuration) within the oral cavity. As noted above, in fact, clearance between the body 12 and the mucosa is needed to allow circulation of the saliva around body 12 to facilitate the release of the medicament therefrom and the application of the medicament to the mucosa.

Figure 6:
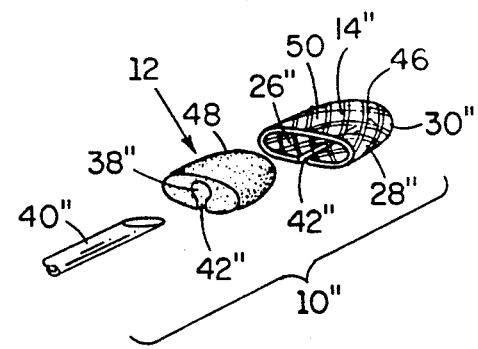
FIG. 6 is a perspective, exploded view of an alternative embodiment of the apparatus of FIG. 1.

Another reason that the apparatus 10 need not be custom built for each patient is that the body 12 is, as noted above, preferably at least somewhat resilient. Even an apparatus such as those having two-piece bodies shown in FIGS. 6 and 7 are characterized by their resilience. Finally, just like the apparatus 10 is resilient in character, the structure of the oral cavity, especially in infants and children, is somewhat resilient. Because of these four factors, it is necessary to provide only four or five different sizes of the body 12 to insure proper function of the apparatus 10 in any patient from a neonate up to about four or five years of age.

Having described the structure of the apparatus 10, reference to that structure will now be made in describing a method of dispensing a medicament in the upper aerodigestive tract of an intubated patient using the apparatus 10. Patient 22 is intubated and the body 12 comprised of a substrate impregnated with the medicament to be delivered in the upper aerodigestive tract of patient 22 is placed onto the tongue 18 of patient 22 by passing the tube 40 of the endotracheal tube 36 with which patient 22 is to be intubated through channel 38, using the slit 42 to slip body 12 over tube 40. Alternatively, the body 12 is introduced into the oral cavity 24 of the patient 22 by placing body 12 on the tongue 18 and the tube 40 of endotracheal tube 36 is then introduced into the oral cavity 24 by passing the tube 40 through the channel 38 of body 12. The body 12 is then stabilized in the oral cavity 24 of the upper aerodigestive tract by engagement of the mucosa of the palate 20 and alveolar ridge 32 and saliva is allowed to circulate around body 12 during normal salivation and/or swallowing to facilitate the release of the medicament therefrom.

Although the invention has been described in terms of the above-characterized, presently preferred embodiments, it will be apparent to those skilled in the art who have the benefit of this disclosure that certain changes in the structure of those embodiments can be made without changing the function of that structure and without departing from the nature and spirit of present invention. All such changes are intended to fall within the scope of the following claims.

What is claimed is:

1. An apparatus for delivery of a medicament in the upper aerodigestive tract of a patient comprising:
    an endotracheal tube;
    a generally ovoid body comprised of a substrate impregnated with a medicament to be delivered in the upper aerodigestive tract of a patient;
    said body having front, side, top and bottom surfaces, the front and side surfaces having a curved and tapered shape for engaging the mucosa of the aveolar ridge and the top surface being shaped for engaging the mucosa of the palate when the bottom surface rests of the tongue of the patient, thereby stabilizing said body in the oral cavity of the patient while allowing sufficient clearance between the mucosa and said body to allow circulation of the saliva around said body to facilitate release of the medicament therefrom; and
    a channel through said body comprising a slit for passage of said endotracheal tube through said body, the endotracheal tube and said channel cooperating with the engagement of the mucosa by said body to stabilize said body and the endotracheal tube in the oral cavity.

2. The apparatus of claim 1 wherein said body is comprised of a silicone-containing elastomer having a medicament impregnated therein.

3. The apparatus of claim 1 wherein the medicament with which said body is impregnated is an antibiotic.

4. The apparatus of claim 1 wherein said body additionally comprises a frame and said substrate is secured to said frame.

5. The apparatus of claim 1 wherein said body additionally comprises a basket and said basket is shaped for receiving said substrate therein.

6. The apparatus of claim 1 additionally comprising a port formed in said body for passage of a tube through said body.

7. The apparatus of claim 1 additionally comprising an extension of said body for delivering the medicament in the pharynx of the upper aerodigestive tract of the patient.

8. The apparatus of claim 1 wherein the substrate is comprised of a silicone containing elastomer having the medicament impregnated therein.

9. The apparatus of claim 1 additionally comprising a basket for receiving the substrate of said body therein.

10. The apparatus of claim 1 additionally comprising an extension from the surface of said body opposite the front surface for delivering the medicament to the pharynx of the upper aerodigestive tract of the patient.

11. The apparatus of claim 1 wherein the top surface of said body is arched to facilitate interdigitation of said body and the inferior aspect of the pharyngeal palate of the patient.

12. The apparatus of claim 1 wherein the slit comprising said channel opens to the surface of said body.

13. The apparatus of claim 1 wherein said substgrate is comprised of a material having a loose construction and said slit is formed by forcing the endotracheal tube therethrough.

14. A method of dispensing a medicament in the upper aerodigestive tract of an intubated patient comprising:
    intubating a patient;
    placing a body comprised of a substrate impregnated with a medicament to be dispensed in the upper aerodigestive tract of the patient onto the tongue of the patient by passing the tube with which the patient is to be intubated therethrough;
    stabilizing the body in the oral cavity of the upper aerodigestive tract by engagement of the mucosa of the palate and alveolar ridge; and
    allowing saliva to circulate around the body to facilitate the release of the medicament therefrom.

15. The method of claim 14 additionally comprising periodically replenishing the medicament released from the body.

16. An apparatus for delivering a medicament in the upper aerodigestive tract of a patient comprising:
    a body formed of a substrate impregnated with a medicament to be delivered in the upper aerodigestive tract of a patient, said substrate being selected so as to release the medicament with which the substrate is impregnated when contacted by an aqueous solution;
    said body having a bottom surface for resting on the tongue of the patient, tapered sides and ends for engaging the mucosa of the alveolar ridge of the patient and a top surface for engaging the mucosa of the palate when the bottom surface of said body rests on the tongue, thereby stabilizing said body in the oral cavity; and
    a channel through said body for passage of an endotracheal tube therethrough to stabilize an endotracheal tube passing therethrough in the oral cavity of the patient by engagement of the mucosa of the oral cavity by the top, bottom and side surfaces of said body.

17. The apparatus of claim 16 wherein said channel opens to the bottom surface of said body through a slit formed in said body.

18. The apparatus of claim 16 wherein the substrate is comprised of an organic polymer or copolymer, silicone elastomer, gel, absorbent material, absorbent natural or synthetic fiber batting or filler, sponge, inert protein, or sugar-based lozenge.

19. The apparatus of claim 16 wherein the top surface of said body is arched for interdigitating with the inferior aspect of the pharyngeal palate of the patient.

20. An apparatus for delivery of a medicament in the upper aerodigestive tract of a patient comprising:
- a body formed of a substrate impregnated with a medicament to be delivered in the upper aerodigestive tract of a patient, said body being shaped for stabilizing said body in the oral cavity of the upper aerodigestive tract of the patient by engaging the mucosa of the palate and the alveolar ridge when said body is placed on the tongue of the patient;
- an extension of said body for dispensing the medicament in the pharynx of the upper aerodigestive tract when said body is placed on the tongue of the patient; and
- means formed in said body for passage of an endotracheal tube therethrough, said tube passage means cooperating with the endotracheal tube to stabilize the endotracheal tube and said body in the oral cavity as a result of the engagement of the mucosa by said body.

21. An apparatus for delivery of a medicament in the upper aerodigestive tract of a patient comprising:
- a body formed of a substrate comprised of a silicone-containing elastomer impregnated with a medicament to be delivered in the upper aerodigestive tract of a patient;
- said body being generally ovoid shaped and having front, side, top, and bottom surfaces, the front and side surfaces for engaging the mucosa of the alveolar ridge and the top surface for engaging the mucosa of the palate when the bottom surface rests on the tongue of the patient, thereby stabilizing said body in the oral cavity of the patient while allowing sufficient clearance between the mucosa and said body to allow circulation of saliva around said body to facilitate the release of the medicament therefrom; and
- means formed in said body for passage of an endotracheal tube therethrough, the endotracheal tube and said tube passage means cooperating with the engagement of the mucosa by said body to stabilize said body and the endotracheal tube in the oral cavity.

22. The apparatus of claim 21 wherein the top surface of said body is arched for interdigitating with the inferior aspect of the pharyngeal palate of the patient.

* * * * *